(12) United States Patent
Liao et al.

(10) Patent No.: US 7,700,775 B2
(45) Date of Patent: *Apr. 20, 2010

(54) COMPOUNDS AND COMPOSITIONS FOR DELIVERING ACTIVE AGENTS

(75) Inventors: Jun Liao, Tarrytown, NY (US); David Gschneidner, Tarrytown, NY (US); John J. Weidner, Tarrytown, NY (US); Nai Fang Wang, Tarrytown, NY (US)

(73) Assignee: Emisphere Technologies, Inc., Tarrytown, NY (US)

( * ) Notice: Subject to any disclaimer, the term of this patent is extended or adjusted under 35 U.S.C. 154(b) by 1900 days.

This patent is subject to a terminal disclaimer.

(21) Appl. No.: 10/469,500

(22) PCT Filed: Mar. 1, 2002

(86) PCT No.: PCT/US02/06610

§ 371 (c)(1),
(2), (4) Date: Aug. 27, 2003

(87) PCT Pub. No.: WO02/069937

PCT Pub. Date: Sep. 12, 2002

(65) Prior Publication Data

US 2004/0097500 A1    May 20, 2004

Related U.S. Application Data

(60) Provisional application No. 60/272,726, filed on Mar. 1, 2001, provisional application No. 60/314,783, filed on Aug. 24, 2001, provisional application No. 60/323,139, filed on Sep. 17, 2001.

(51) Int. Cl.
*C07C 233/00* (2006.01)

(52) U.S. Cl. .......... 546/167; 544/169; 544/222; 544/388; 544/391; 546/337; 548/346.1

(58) Field of Classification Search .......... 424/464; 514/211.05; 546/167, 337; 544/169, 222, 544/388, 391; 548/346.1
See application file for complete search history.

(56) References Cited

U.S. PATENT DOCUMENTS

| 2,810,718 | A | * | 10/1957 | Swett et al. .......... 544/169 |
| 3,455,940 | A | * | 7/1969 | Stecker .......... 546/337 |
| 4,464,363 | A | | 8/1984 | Higuchi et al. |
| 4,470,980 | A | | 9/1984 | Higuchi et al. |
| 5,583,020 | A | | 12/1996 | Sullivan |
| 6,344,449 | B1 | * | 2/2002 | Rudolf et al. .......... 514/211.05 |
| 6,399,798 | B2 | * | 6/2002 | Gschneidner et al. .......... 554/35 |
| 6,646,162 | B2 | * | 11/2003 | Tang et al. .......... 564/167 |

FOREIGN PATENT DOCUMENTS

| GB | 862721 | 3/1961 |
| GB | 874206 | 8/1961 |
| WO | 00/50386 A1 | 8/2000 |
| WO | 01/44199 A1 | 6/2001 |

OTHER PUBLICATIONS

CL. Baldazzi et al.: "A New Series of 6-Chloro-2, 3-Dihydro-4(1H)-Quinazolinone Derivatives As Antiemetic A. Gastrointestinal Motility Enhancing Agents." Arzneimittel Forschung. Drug Research., vol. 46, No. 9, 1996, pp. 911-918, XP002445072, Deecv Editio Cantor Verlag, Aulendorf.

* cited by examiner

*Primary Examiner*—Kevin Weddington
(74) *Attorney, Agent, or Firm*—Darby & Darby

(57) ABSTRACT

Compounds and compositions for the delivery of active agents are provided. Methods of administration and preparation are provided as well.

11 Claims, No Drawings

COMPOUNDS AND COMPOSITIONS FOR DELIVERING ACTIVE AGENTS

This application is the National Stage of International Application No. PCT/US02/06610, filed Mar. 1, 2002, which claims the benefit of U.S. Provisional Application No. 60/272,726, filed Mar. 1, 2001; U.S. Provisional Application No. 60/314,783, filed Aug. 24, 2001; and U.S. Provisional Application No. 60/323,139, filed Sep. 17, 2001, all of which are hereby incorporated by reference.

FIELD OF THE INVENTION

The present invention relates to compounds for delivering active agents, such as biologically or chemically active agents, to a target. These compounds are well suited for forming non-covalent mixtures with active agents for oral, intracolonic, pulmonary, and other routes of administration to animals. Methods for the preparation and administration of such compositions are also disclosed.

BACKGROUND OF THE INVENTION

Conventional means for delivering active agents are often severely limited by biological, chemical, and physical barriers. Typically, these barriers are imposed by the environment through which delivery occurs, the environment of the target for delivery, and/or the target itself. Biologically and chemically active agents are particularly vulnerable to such barriers.

In the delivery to animals of biologically active and chemically active pharmacological and therapeutic agents, barriers are imposed by the body. Examples of physical barriers are the skin, lipid bi-layers and various organ membranes that are relatively impermeable to certain active agents but must be traversed before reaching a target, such as the circulatory system. Chemical barriers include, but are not limited to, pH variations in the gastrointestinal (GI) tract and degrading enzymes.

These barriers are of particular significance in the design of oral delivery systems. Oral delivery of many biologically or chemically active agents would be the route of choice for administration to animals if not for biological, chemical, and physical barriers. Among the numerous agents which are not typically amenable to oral administration are biologically or chemically active peptides, such as calcitonin and insulin; polysaccharides, and in particular mucopolysaccharides including, but not limited to, heparin; heparinoids; antibiotics; and other organic substances. These agents may be rapidly rendered ineffective or destroyed in the gastro-intestinal tract by acid hydrolysis, enzymes, and the like. In addition, the size and structure of macromolecular drugs may prohibit absorption.

Earlier methods for orally administering vulnerable pharmacological agents have relied on the co-administration of adjuvants (e.g., resorcinols and non-ionic surfactants such as polyoxyethylene oleyl ether and n-hexadecylpolyethylene ether) to increase artificially the permeability of the intestinal walls, as well as the co-administration of enzymatic inhibitors (e.g., pancreatic trypsin inhibitors, diisopropylfluorophosphate (DFF) and trasylol) to inhibit enzymatic degradation. Liposomes have also been described as drug delivery systems for insulin and heparin. However, broad spectrum use of such drug delivery systems is precluded because: (1) the systems require toxic amounts of adjuvants or inhibitors; (2) suitable low molecular weight cargos, i.e. active agents, are not available; (3) the systems exhibit poor stability and inadequate shelf life; (4) the systems are difficult to manufacture; (5) the systems fail to protect the active agent (cargo); (6) the systems adversely alter the active agent; or (7) the systems fail to allow or promote absorption of the active agent.

Proteinoid microspheres have been used to deliver pharmaceuticals. See, for example, U.S. Pat. Nos. 5,401,516; 5,443,841; and Re. 35,862. In addition, certain modified amino acids have been used to deliver pharmaceuticals. See, for example, U.S. Pat. Nos. 5,629,020; 5,643,957; 5,766,633; 5,776,888; and 5,866,536.

More recently, a polymer has been conjugated to a modified amino acid or a derivative thereof via a linkage group to provide for polymeric delivery agents. The modified polymer may be any polymer, but preferred polymers include, but are not limited to, polyethylene glycol (PEG), and derivatives thereof. See, for example, International Patent Publication No. WO 00/40203.

However, there is still a need for simple, inexpensive delivery systems which are easily prepared and which can deliver a broad range of active agents by various routes.

SUMMARY OF THE INVENTION

The present invention provides compounds and compositions which facilitate the delivery of active agents. Delivery agent compounds of the present invention include those having the following formulas:

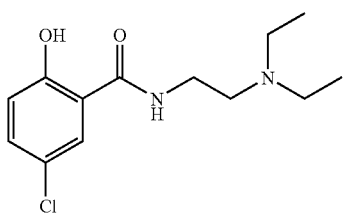

Compound 1

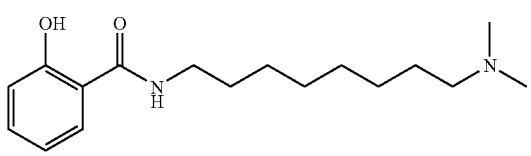

Compound 2

-continued
Compound 3
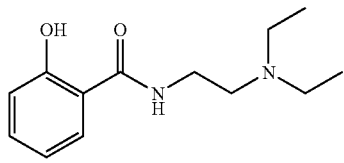
Compound 4
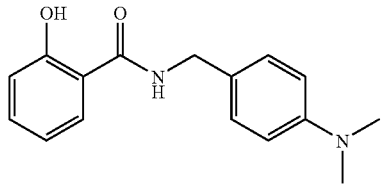
Compound 5
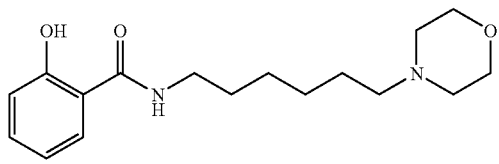
Compound 6
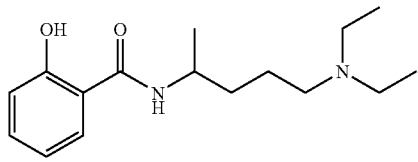
Compound 7
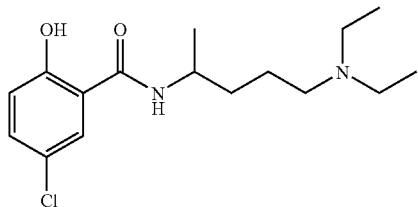
Compound 8
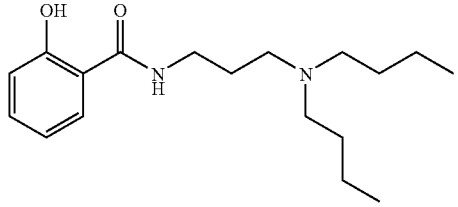
Compound 9
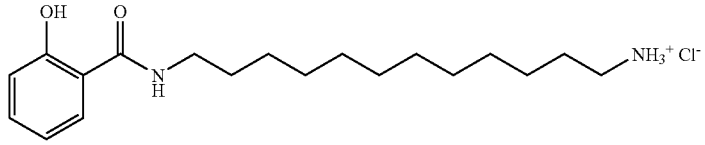
Compound 10
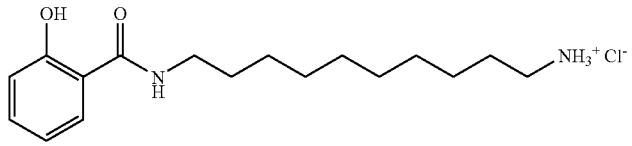
Compound 11
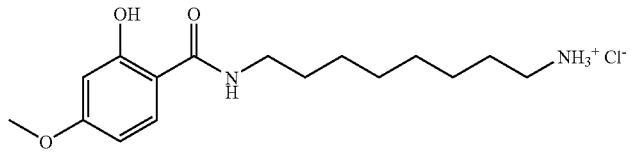

-continued

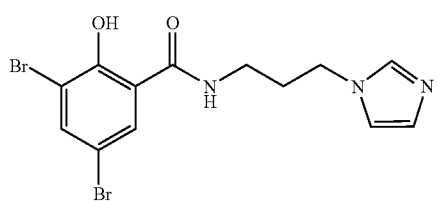
Compound 12

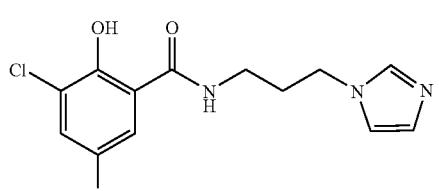
Compound 13

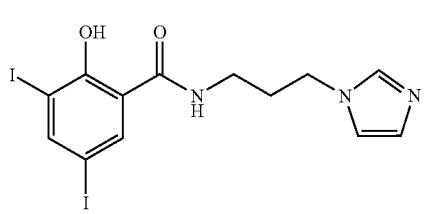
Compound 14

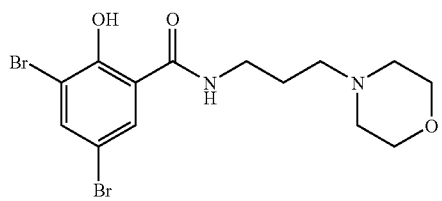
Compound 15

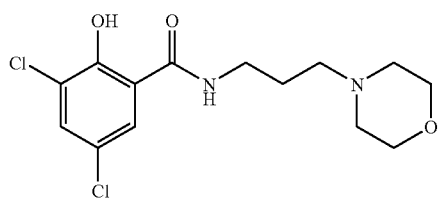
Compound 16

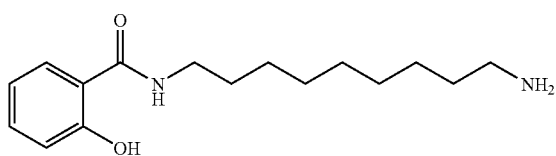
Compound 17

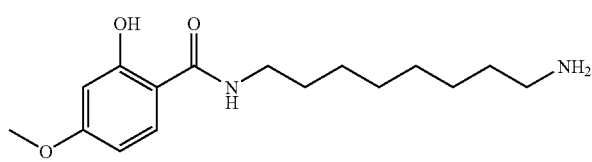
Compound 18 and salts thereof. Mixtures of these delivery agent compounds may also be used to facilitate the delivery of active agents.

The invention also provides a composition comprising at least one of the delivery agent compounds of the formulas above, and at least one active agent. These compositions deliver active agents to selected biological systems in increased or improved bioavailability of the active agent compared to administration of the active agent without the delivery agent compound.

Also provided are dosage unit forms comprising the compositions. The dosage unit may be in the form of a liquid or a solid, such as a tablet, capsule or particle, including a powder or sachet.

Another embodiment is a method for administering an active agent to an animal in need of the active agent, by administering a composition comprising at least one of the delivery agent compounds of the formula above and the active agent to the animal. Preferred routes of administration include the oral, intracolonic and pulmonary routes.

Yet another embodiment is a method of treating a disease or for achieving a desired physiological effect in an animal by administering the composition of the present invention.

Yet another embodiment is a method of preparing a composition of the present invention by mixing at least one delivery agent compound of the formula above, and at least one active agent.

DETAILED DESCRIPTION OF THE INVENTION

Delivery Agent Compounds

The terms "alkyl" and "alkenyl" as used herein include linear and branched alkyl and alkenyl substituents, respectively.

The delivery agent compounds may be in the form of the free base or salts thereof. Suitable salts include, but are not limited to, organic and inorganic salts, for example, hydrochloride, ammonium, acetate, citrate, halide, hydroxide, sulfate, nitrate, phosphate, alkoxy, perchlorate, tetrafluoroborate, carboxylate, mesylate, fumerate, malonate, succinate, tartrate, acetate, gluconate, and maleate salts. The salts may also be solvates, including ethanol solvates, and hydrates. The mesylate salt can be formed by reacting the free base of the delivery agent compound with methanesulfonic acid.

Salts of the delivery agent compounds of the present invention may be prepared by methods known in the art. For example, citrate salts may be prepared in ethanol, toluene and citric acid. The salts may also be solvates, including ethanol solvates, and hydrates.

The delivery agent compound may be purified by recrystallization or by fractionation on one or more solid chromatographic supports, alone or linked in tandem. Suitable recrystallization solvent systems include, but are not limited to, ethanol, water, heptane, ethyl acetate, acetonitrile, methanol, and tetrahydrofuran (THF) and mixtures thereof. Fractionation may be performed on a suitable chromatographic support such as alumina, using methanol/n-propanol mixtures as the mobile phase; reverse phase chromatography using trifluoroacetic acid/acetonitrile mixtures as the mobile phase; and ion exchange chromatography using water or an appropriate buffer as the mobile phase. When anion exchange chromatography is performed, preferably a 0-500 mM sodium chloride gradient is employed.

The delivery agent may contain a polymer conjugated to it by a linkage group selected from the group consisting of —NHC(O)NH—, —C(O)NH—, —NHC(O), —OOC—, —COO—, —NHC(O)O—, —OC(O)NH—, —CH$_2$NH —NHCH$_2$—, —CH$_2$NHC(O)O—, —OC(O)NHCH$_2$—, —CH$_2$NHCOCH$_2$O—, —OCH$_2$C(O)NHCH$_2$—, —NHC (O)CH$_2$O—, —OCH$_2$C(O)NH—, —NH—, —O—, and carbon-carbon bond, with the proviso that the polymeric delivery agent is not a polypeptide or polyamino acid. The polymer may be any polymer including, but not limited to, alternating copolymers, block copolymers and random copolymers, which are safe for use in mammals. Preferred polymers include, but are not limited to, polyethylene; polyacrylates; polymethacrylates; poly(oxyethylene); poly(propylene); polypropylene glycol; polyethylene glycol (PEG); and derivatives thereof and combinations thereof. The molecular weight of the polymer typically ranges from about 100 to about 200,000 daltons. The molecular weight of the polymer preferably ranges from about 200 to about 10,000 daltons. In one embodiment, the molecular weight of the polymer ranges from about 200 to about 600 daltons and more preferably ranges from about 300 to about 550 daltons.

Active Agents

Active agents suitable for use in the present invention include biologically active agents and chemically active agents, including, but not limited to, pesticides, pharmacological agents, and therapeutic agents. Suitable active agents include those that are rendered less effective, ineffective or are destroyed in the gastro-intestinal tract by acid hydrolysis, enzymes and the like. Also included as suitable active agents are those macromolecular agents whose physiochemical characteristics, such as, size, structure or charge, prohibit or impede absorption when dosed orally.

For example, biologically or chemically active agents suitable for use in the present invention include, but are not limited to, proteins; polypeptides; peptides; hormones; polysaccharides, and particularly mixtures of mucopolysaccharides; carbohydrates; lipids; small polar organic molecules (i.e. polar organic molecules having a molecular weight of 500 daltons or less); other organic compounds; and particularly compounds which by themselves do not pass (or which pass only a fraction of the administered dose) through the gastro-intestinal mucosa and/or are susceptible to chemical cleavage by acids and enzymes in the gastrointestinal tract; or any combination thereof.

Further examples include, but are not limited to, the following, including synthetic, natural or recombinant sources thereof: growth hormones, including human growth hormones (hGH), recombinant human growth hormones (rhGH), bovine growth hormones, and porcine growth hormones; growth hormone releasing hormones; growth hormone releasing factor, interferons, including $\alpha$, $\beta$ and $\gamma$; interleukin-1; interleukin-2; insulin, including porcine, bovine, human, and human recombinant, optionally having counter ions including zinc, sodium, calcium and ammonium; insulin-like growth factor, including IGF-1; heparin, including unfractionated heparin, heparinoids, dermatans, chondroitins, low molecular weight heparin, very low molecular weight heparin and ultra low molecular weight heparin; calcitonin, including salmon, eel, porcine and human; erythropoietin; atrial naturetic factor; antigens; monoclonal antibodies; somatostatin; protease inhibitors; adrenocorticotropin, gonadotropin releasing hormone; oxytocin; leutinizing-hormone-releasing-hormone; follicle stimulating hormone; glucocerebrosidase; thrombopoietin; filgrastim; prostaglandins; cyclosporin; vasopressin; cromolyn sodium (sodium or disodium chromoglycate); vancomycin; desferrioxamine (DFO); bisphosphonates, including alendronate, tiludronate, etidronate, clodronate, pamidronate, olpadronate, and incadronate; parathyroid hormone (PTH), including its fragments; anti-migraine agents such as BIBN-4096BS and other calcitonin gene-related proteins antagonists; antimicrobials, including antibiotics, anti-bacterials and anti-fungal agents; vitamins; analogs, fragments, mimetics or polyethylene glycol (PEG)-modified derivatives of these compounds; or any combination thereof. Non-limiting examples of antibiotics include gram-positive acting, bacteriocidal, lipopeptidal and cyclic peptidal antibiotics, such as daptomycin and analogs thereof.

Delivery Systems

The composition of the present invention comprises one or more delivery agent compounds of the present invention, and one or more active agents. In one embodiment, one or more of the delivery agent compounds, or salts of these compounds, or poly amino acids or peptides of which these compounds or salts form one or more of the units thereof, may be used as a delivery agent by mixing with the active agent prior to administration to form an administration composition.

The administration compositions may be in the form of a liquid. The solution medium may be water (for example, for salmon calcitonin, parathyroid hormone, and erythropoietin), 25% aqueous propylene glycol (for example, for heparin) and phosphate buffer (for example, for rhGH). Other dosing vehicles include polyethylene glycol. Dosing solutions may be prepared by mixing a solution of the delivery agent compound with a solution of the active agent, just prior to administration. Alternately, a solution of the delivery agent compound (or active agent) may be mixed with the solid form of the active agent (or delivery agent compound). The delivery agent compound and the active agent may also be mixed as dry powders. The delivery agent compound and the active agent can also be admixed during the manufacturing process.

The dosing solutions may optionally contain additives such as phosphate buffer salts, citric acid, glycols, or other dispersing agents. Stabilizing additives may be incorporated into the solution, preferably at a concentration ranging between about 0.1 and 20% (w/v).

In one embodiment, dosing solution containing BIBN-4096BS have a pH of less than 8. According to another embodiment, dosing solutions containing BIBN-4096BS have a pH of less than 7.

The administration compositions may alternately be in the form of a solid, such as a tablet, capsule or particle, such as a powder or sachet. Solid dosage forms may be prepared by mixing the solid form of the compound with the solid form of the active agent. Alternately, a solid may be obtained from a solution of compound and active agent by methods known in the art, such as freeze-drying (lyophilization), precipitation, crystallization and solid dispersion.

The administration compositions of the present invention may also include one or more enzyme inhibitors. Such enzyme inhibitors include, but are not limited to, compounds such as actinonin or epiactinonin and derivatives thereof. Other enzyme inhibitors include, but are not limited to, aprotinin (Trasylol) and Bowman-Birk inhibitor.

The amount of active agent used in an administration composition of the present invention is an amount effective to accomplish the purpose of the particular active agent for the target indication. The amount of active agent in the compositions typically is a pharmacologically, biologically, therapeutically, or chemically effective amount. However, the amount can be less than that amount when the composition is used in a dosage unit form because the dosage unit form may contain a plurality of delivery agent compound/active agent compositions or may contain a divided pharmacologically, biologically, therapeutically, or chemically effective amount. The total effective amount can then be administered in cumulative units containing, in total, an effective amount of the active agent.

The total amount of active agent to be used can be determined by methods known to those skilled in the art. However, because the compositions of the invention may deliver active agents more efficiently than compositions containing the active agent alone, lower amounts of biologically or chemically active agents than those used in prior dosage unit forms or delivery systems can be administered to the subject, while still achieving the same blood levels and/or therapeutic effects.

The presently disclosed delivery agent compounds facilitate the delivery of biologically and chemically active agents, particularly in oral, intranasal, sublingual, intraduodenal, subcutaneous, buccal, intracolonic, rectal, vaginal, mucosal, pulmonary, transdermal, intradermal, parenteral, intravenous, intramuscular and ocular systems, as well as traversing the blood-brain barrier.

Dosage unit forms can also include any one or combination of excipients, diluents, disintegrants, lubricants, plasticizers, colorants, flavorants, taste-masking agents, sugars, sweeteners, salts, and dosing vehicles, including, but not limited to, water, 1,2-propane diol, ethanol, olive oil, or any combination thereof.

The compounds and compositions of the subject invention are useful for administering biologically or chemically active agents to any animals, including but not limited to birds such as chickens; mammals, such as rodents, cows, pigs, dogs, cats, primates, and particularly humans; and insects.

The system is particularly advantageous for delivering chemically or biologically active agents that would otherwise be destroyed or rendered less effective by conditions encountered before the active agent reaches its target zone (i.e. the area in which the active agent of the delivery composition is to be released) and within the body of the animal to which they are administered. Particularly, the compounds and compositions of the present invention are useful in orally administering active agents, especially those that are not ordinarily orally deliverable, or those for which improved delivery is desired.

The compositions comprising the compounds and active agents have utility in the delivery of active agents to selected biological systems and in an increased or improved bioavailability of the active agent compared to administration of the active agent without the delivery agent. Delivery can be improved by delivering more active agent over a period of time, or in delivering active agent in a particular time period (such as to effect quicker or delayed delivery), or in delivering the active agent at a specific time, or over a period of time (such as sustained delivery).

Another embodiment of the present invention is a method for the treatment or prevention of a disease or for achieving a desired physiological effect, such as those listed in the table below, in an animal by administering the composition of the present invention. Specific indications for active agents can be found in the Physicians' Desk Reference (54$^{th}$ Ed., 2000, Medical Economics Company, Inc., Montvale, N.J.), which is herein incorporated by reference. The active agents in the table below include their analogs, fragments, mimetics, and polyethylene glycol-modified derivatives.

| Active Agent | Disease and Physiological Effect |
| --- | --- |
| Growth hormones | Growth disorders |
| Interferons, including $\alpha$, $\beta$ and $\gamma$. | Viral infection, including chronic cancer and multiple sclerosis |
| Interleukin-1; interleukin-2. | Viral infection; cancer |
| Insulin; Insulin-like growth factor IGF-1. | Diabetes |
| Heparin | Thrombosis; prevention of blood coagulation |
| Calcitonin. | Osteoporosis; diseases of the bone |
| Erythropoietin | Anemia |
| Atrial naturetic factor | Vasodilation |
| Antigens | Infection |
| Monoclonal antibodies | To prevent graft rejection; cancer |
| Somatostatin | Bleeding ulcer; erosive gastritis |
| Protease inhibitors | AIDS |
| Adrenocorticotropin | High cholesterol (to lower cholesterol) |
| Gonadotropin releasing hormone | Ovulatory disfunction (to stimulate ovulation) |

-continued

| Active Agent | Disease and Physiological Effect |
|---|---|
| Oxytocin | Labor disfunction (to stimulate contractions) |
| Leutinizing-hormone-releasing-hormone; follicle stimulating hormone | Regulate reproductive function |
| Glucocerebrosidase | Gaucher disease (to metabolize lipoprotein) |
| Thrombopoietin | Thrombocytopenia |
| Filgrastim | Reduce infection in chemotherapy patients |
| Prostaglandins | Hypertension |
| Cyclosporin | Transplant rejection |
| Vasopressin | Bed-wetting; antidiuretic |
| Cromolyn sodium; Vancomycin | Asthma; allergies |
| Desferrioxamine (DFO) | Iron overload |
| Parathyroid hormone (PTH), including its fragments. | Osteoporosis; Diseases of the bone |
| Antimicrobials | Infection including gram-positive bacterial infection |
| Vitamins | Vitamin deficiencies |
| Bisphosphonates | Osteoporosis; Paget's disease; Inhibits osteoclasts |
| BIBN4096BS - (1-Piperidinecarboxamide. N-[2-[[5-amino-1-[[4-(4-pyridinyl)-1-piperazinyl)carbonyl]pentyl]amino]-1-[(3,5-dibromo-4-hydroxyphenyl)methyl]-2-oxoethyl]-4(1,4-dihydro-2-oxo-3(2H0-quinazolinyl)-.[R-(R*,S*)]-) | Anti-migraine; calcitonin gene-related peptide antagonist |

For example, one embodiment of the present invention is a method for treating a patient suffering from or susceptible to diabetes by administering insulin and at least one of the delivery agent compounds of the present invention.

Following administration, the active agent present in the composition or dosage unit form is taken up into the circulation. The bioavailability of the agent is readily assessed by measuring a known pharmacological activity in blood, e.g. an increase in blood clotting time caused by heparin, or a decrease in circulating calcium levels caused by calcitonin. Alternately, the circulating levels of the active agent itself can be measured directly.

DESCRIPTION OF THE PREFERRED EMBODIMENTS

The following examples illustrate the invention without limitation. All parts are given by weight unless otherwise indicated.

Proton nuclear magnetic resonance ($^1$H NMR) analyses for the compounds listed below were conducted on a 300 MHz Bruker spectrometer using dimethyl sulfoxide (DMSO-$d_6$) as the solvent unless otherwise indicated.

Liquid chromatograph/mass spectrometry (LC-MS) analyses were performed with an Agilent Technologies, LC/MSD 1100 (single quad) having the following parameters:

Mobile Phase A: 50:950:5 acetonitrile:water:acetic acid (v/v/v)
Mobile Phase B: 950:50:5 acetonitrile:water:acetic acid (v/v/v)
Gradient Elution: 4 minute linear gradient 0-100% B; total time per injection is 11 minutes
Injection volume: 5 uL
Column: ZORBAX Rapid Resolution Cartridge, SB-C18, 2.1×30 mm, 3.5 um
Particle size, catalog # 873700-902
Column temp: 40° C.
UV detection at 244 nm
MSD parameters:
Source: API-ES, positive polarity
Scan Parameters:
  Mass Range: 125.00-600.00
  Fragmentor: 60 V
  Gain: 1.0 EMV
  Threshold: 150
Spray Chamber:
  Gas Temp. 350 deg. D
  Drying Gas: 12.0 l/min
  Neb. Pressure; 40 psig
  VCap 4000V positive/negative

EXAMPLE 1

Preparation of Compounds

1a: Preparation of Compound 2

A solution of 40% dimethylamine/water (30 mL, 26.9 g, 239 mmol) and ethanol (50 mL) was treated with a solution of 8-bromo-1-octanol (15.13 g, 72.3 mmol) and ethanol (20 mL), added dropwise over 10 minutes. The reaction mixture was stirred for 75 hours, diluted with ethyl acetate (80 mL) and washed with saturated sodium bicarbonate solution. The aqueous phase was extracted with ethyl acetate. The combined organic phases were washed with saturated sodium bicarbonate solution (50 mL) and brine (2×40 mL), dried over sodium sulfate, and concentrated. The 11.4 g of 8-dimethylamino-1-octanol, isolated as a yellow oil, was used as is.

A slurry of carsalam (10.80 g, 66.2 mmol), 8-dimethylamino-1-octanol (11.4 g, 65.8 mmol), triphenylphosphine (17.53 g, 66.8 mmol) and tetrahydrofuran (40 mL) was treated with a solution of diisopropyl azodicarboxylate (13.0 mL, 13.35 g, 66.0 mmol) and tetrahydrofuran (20 mL,), added dropwise over 25 minutes causing the temperature to rise to 50° C. The reaction mixture was allowed to cool back to 25° C. and stirred for 40 hours. The solution was treated with aqueous 2N NaOH (70 mL, 140 mmol) and warmed to 60° C. for 180 minutes. The cooled reaction mixture was washed with ethyl acetate (2×50 mL). The aqueous phase was acidified with 4% aqueous HCl to a pH slightly less than 0 and was washed with ethyl acetate (2×40 mL). The pH of the aqueous phase was raised to 9.5 upon treatment with solid sodium bicarbonate. The aqueous phase was extracted with methylene chloride (10×40 mL). The combined methylene chloride extracts were dried over sodium sulfate and concentrated to give 0.6 g of product. The rest of the product was found in the earlier ethyl acetate extracts. These ethyl acetate layers were extracted with 1N aqueous NaOH (4×30 mL). These 4 aqueous phases were combined, acidified to pH 0.7 with 4% aqueous HCl, and washed with ethyl acetate (2×30 mL). The pH of the aqueous solution was adjusted to 5 with aqueous 2N NaOH. The solution was treated with solid sodium bicarbonate until no more bubbling occurred and was extracted with ethyl acetate (6×50 mL). The combined ethyl acetate layers were dried over sodium sulfate and concentrated to a solid. The solid was taken up into a tetrahydrofuran and treated with HCl gas. Water was added causing a solid to precipitate out of solution. A total of 4.73 g of N-(8-dimethylaminooctyl)salicylamide hydrochloride was isolated by filtration.

m.p. 78-80° C.; $^1$H NMR (DMSO-$d_6$), δ (ppm): 10.5 (bs, 1H), 8.9 (t, 1H), 7.9 (dd, 1H), 7.4 (td, 1H), 6.9 (m, 2H), 3.3 (q, 2H), 3.0 (m, 2H), 2.7 (s, 6H), 1.6 (t, 4H), 1.3 (m, 8H). KF value=5.19% water. Elemental analysis: % C: 58.86 (calculated), 58.87 (found); % H: 9.01 (calculated), 8.98 (found); % N: 8.08 (calculated), 7.98 (found).

1b: Preparation of Compound 4

A one-neck, 250 mL round bottomed flask was charged with 4-(dimethylamino)benzylamine dihydrochloride (8.0 g, 0.0358 mol) and 50 mL of methylene chloride. The stirred solution was chilled in an ice bath. Triethylamine (20.0 mL, 0.1432 mol) and a catalytic amount of 4-(dimethylamino) pyridine (DMAP) were added to the reaction mixture. A solution of acetylsalicyloyl chloride (7.12 g, 0.1432 mol) in methylene chloride (30 mL) was added to the chilled reaction flask. After the addition was complete, the reaction mixture was warmed to room temperature and was allowed to stir overnight.

The reaction mixture was diluted with 2N HCl, and the layers were separated. The organic phase was washed with water, dried over sodium sulfate, and concentrated in vacuo. The resulting oil was stirred in 2N NaOH for 4 hours, and washed with ethyl acetate. The aqueous phase was concentrated in vacuo to remove any residual ethyl acetate. The pH of the aqueous phase was adjusted to 7, and the resulting solids were collected by vacuum filtration. The weight of the crude solids was 1.76 g. The reaction was repeated to give an additional 0.88 g of crude product. The combined solids were recrystallized from ethanol/water to give 2.64 g of N-(4-dimethylaminobenzyl) salicylamide as a white solid.

m.p. 129-132° C.; $^1$H NMR (d$_6$-DMSO), δ (ppm): 9.3 (s, 1H), 7.87 (dd, 1H), 7.39 (dt, 1H), 7.16 (d, 2H), 6.87 (t, 2H), 6.69 (d, 2H), 4.38 (d, 2H), 2.86 (s, 6H). Elemental analysis: % C: 71.09 (calc.), 70.84 (found); % H: 6.71 (calc.), 6.50 (found); % N, 10.36 (calc.), 10.14 (found).

1c: Preparation of Compound 5

A suspension of morpholine (3.30 mL, 3.30 g, 37.8 mmol), 6-bromo-1-hexanol (6.72 g, 72.3 mmol), ethanol (20 mL), and potassium carbonate (6.23 g, 45.1 mmol) was stirred for 36 hours at 25° C., after a slight exotherm at the beginning. The reaction mixture was diluted with ethyl acetate (30 mL), filtered and concentrated. The residue was taken up in ethyl acetate, filtered and concentrated. The 7.0 g of 4-(6-hydroxyhexyl)morpholine was isolated as a yellow oil and used as is.

A slurry of carsalam (6.13 g, 37.6 mmol), 4-(6-hydroxyhexyl)morpholine (7.0 g, 37.4 mmol), triphenylphosphine (9.97 g, 35.0 mmol), and tetrahydrofuran (40 mL) was treated with a solution of diisopropyl azodicarboxylate (7.40 mL, 7.60 g, 37.6 mmol) and tetrahydrofuran (10 mL), added dropwise over 15 minutes. The reaction mixture was stirred at 25° C. for 60 hours. The solution was treated with aqueous 2N NaOH (50 mL, 100 mmol) and warmed to 60° C. for 180 minutes. The cooled reaction mixture was concentrated to remove the tetrahydrofuran. The aqueous residue was washed with ethyl acetate (2×40 mL), and was acidified with 4% aqueous HCl to a pH of 0.84 (causing carbon dioxide gas to evolve). The pH of the aqueous phase was raised to 7.8 with 2N aqueous NaOH. Solid sodium bicarbonate was added. Extraction with ethyl acetate (8×40 mL), drying over sodium sulfate and concentration gave an oil which solidified upon standing. A total of 4.26 g of 4-(6-morpholin-4-ylhexyl)-salicylamide was isolated.

m.p. 70-73° C.; $^1$H NMR (d$_6$-DMSO), δ (ppm): 8.8 (t, 1H), 7.8 (dd, 1H), 7.4 (td, 1H), 6.9 (m, 2H), 3.5 (t, 4H), 3.3 (q, 2H), 2.3 (t, 4H), 2.2, (t, 2H), 1.5 (t, 2H), 1.3-1.4 (m, 6H). KF value=5.39% water. Elemental analysis: % C: 63.05 (calculated), 63.06 (found); % H: 8.70 (calculated), 8.53 (found); % N: 8.65 (calculated), 8.73 (found).

1d: Preparation of the Citrate Salts of Compounds 1,7

Synthesis of N-Hydroxysuccimide-O-acetyl-5-chlorosalicylate

5-Chlorosalicylic acid (17.3 g, 100 mmol) and three drops of concentrated sulfuric acid (98%) were added to a solution of acetic anhydride (14 g, 137 mmol) and glacial acetic acid (16.4 g, 274 mmol) with stirring. The reaction mixture was slowly heated to 70° C. and stirred for 2 hours. The reaction mixture was cooled to room temperature and was gradually added to ice water (500 mL) to precipitate the acetylated product. These solids were collected and washed with water. The two batches of product were combined and recrystallized in ethyl acetate. The pure crystals were collected via vacuum filtration to give 16.3 g of O-acetyl-5-chlorosalicylic acid (76 mmol, 76% yield).

Elemental analysis calculated for $C_9H_7O_4Cl$: C 50.37%, H 3.29%, N 0.0%; Found: C 50.36%, H 3.20%, N<0.02%.

N-Hydroxysuccinimide (8.6 g, 82 mmol) was dissolved in dimethyl formamide (DMF) (8 mL). This solution was mixed with O-Acetyl-5-chlorosalicylic acid (16 g, 74.6 mmol) in dichloromethane (DCM) (150 mL) at room temp. This mixture was stirred in a water bath. 1,3-dicyclohexylcarbodiimide (DCC) (17 g, 82 mmol) was dissolved in dichloromethane (55 mL) and was gradually added to the mixture. The reaction equilibrated to room temperature and stirred for 24 hours. The mixture was cooled to −10° C. and was filtered to remove any solids. The filtrate was diluted with dichloromethane (100 mL). The solution was washed with 1N HCl (2×200 mL), brine (2×200 mL), 5% sodium bicarbonate (2×200 mL) and brine (2×200 mL). The dichloromethane layer was dried over anhydrous sodium sulfate. The solvent was evaporated in vacuo. The product was collected to give 22.5 g (72 mmol, 97%).

Compound 7: 2-(5-chloro-2-hydroxybenzoyl)amino-5-(N', N'-diethylamino)pentane Mono-citrate IUPAC name: N-[5-(diethylamino)-1-methylpentyl]-5-chloro-2-hydroxybenzamide Mono-citrate N-Hydroxysuccimide-O-acetyl-5-chlorosalicylate obtained above (3.1 g, 10 mmol) was dissolved in dichloromethane (15 mL). This solution was slowly added to 2-amino-5-diethylaminopentane (3.2 g, 20 mmol) in dichloromethane (35 mL) with stirring. The reaction mixture was stirred overnight at room temperature. HPLC indicated the completion of the reaction. The reaction mixture was washed with 5% sodium bicarbonate (3×100 mL). The organic layer was dried over anhydrous sodium sulfate. The dichloromethane evaporated in vacuo to give the free tertiary amine product (2.3 g, 7.4 mmol, 74%).

The above obtained 2-(5-chloro-2-hydroxybenzoylamino)-5-(N,N-diethylamino)pentane (2.3 g, 7.4 mmol) and citric acid (1.4 g, 7.4 mmol) were dissolved in anhydrous ethyl alcohol (8 mL). Diethylether (~30 mL) was added to this solution until the solution became cloudy. The cloudy solution was refrigerated overnight to precipitate the citric acid salt. The final product, 2-(5-chloro-2-hydroxybenzoylamino)-5-(N,N-diethylamino)pentane mono-citrate, was collected via vacuum filtration and dried under nitrogen flow to give 2.0 g (4.0 mmol, 54%).

m.p. 57-59° C.; $^1$HNMR (DMSO-d$_6$) δ (ppm): 1.18 (m, 9H), 1.60 (m, 4H), 2.57 (q$_{ab}$, 4H), 3.08 (m, 6H), 4.04 (q, 1H), 4.11 (s, 1H), 6.98 (d, 1H), 7.47 (dd, 1H), 8.01 (d, 1H), 8.70 (s, 1H). KF value=0.59%. Elemental analysis for calculated $C_{22}H_{33}N_2O_9Cl$: C 52.33, H 6.54, N 5.55. Found: C 52.21, H 6.79, N 5.20.

Compound 1: N-(5-chloro-2-hydroxybenzoyl)-N',N'-diethylenediamine Mono-citrate

IUPAC name: N-[2-(diethylamino)ethyl]-5-chloro-2-hydroxybenzamide Mono-citrate

Compound 1 was prepared by the same procedure as for compound 7 with the appropriate starting materials.

m.p. 107-109° C.; $^1$HNMR (DMSO-d$_6$), δ (ppm): 1.16 (t, 6H), 2.61 (q$_{ab}$, 4H), 3.09 (m, 6H), 3.59 (s, 2H), 6.98 (d, 1H), 7.44 (dd, 1H), 7.88 (d, 1H), 9.09 (s, 1H), 9.95-11.20 (s, 3H). Elemental analysis for calculated C$_{19}$H$_{27}$N$_2$O$_9$Cl: C 49.30, H 5.84, N 6.05; found: C 49.30, H 5.78, N 5.94.

1e: Preparation of Compound 11,18

Synthesis of N-Hydroxysuccimide-O-acetyl-4-methoxysalicylate

N-hydroxysuccimide-O-acetyl-4-methoxysalicylate was prepared by the same procedure as for N-hydroxy-O-acetyl-5-chlorosalicylate with the appropriate starting materials.

Compound 11: 8-(2-hydroxy-4-methoxybenzoylamido) Octylamine Hydrogen Chloride

IUPAC name: N-(8-aminooctyl)-2-hydroxy-4-methoxybenzamide Hydrogen Chloride

N-hydroxysuccimide-O-acetyl-4-methoxysalicylate as obtained above (13 g, 42.3 mmol) was dissolved in dichloromethane (70 mL) and added dropwise to a solution of 1,8-diaminooctane (13 g, 90 mmol) in dichloromethane (230 mL) in a water bath with stirring. The reaction was stirred overnight. The product precipitated out of solution and was collected via vacuum filtration. The precipitates were washed with dichloromethane and were air-dried to give 9.0 g of crude product. The precipitates were washed with water (50 mL) and extracted with 0.1N HCl aqueous solution (50 mL) for 0.5 hours with stirring. The acidic aqueous solution was filtered to remove insoluble material. The filtrate was washed with ethyl ether (150 mL) and was adjusted to pH 10. Precipitation occurred immediately. The mixture was allowed to stand at room temperature over night. The precipitate was collected by filtration and air-dried to yield 2.6 g (8.8 mmol, 21%).

The free primary amine obtained above (1.7 g, 5.8 mmol) was suspended in 20 mL of anhydrous ethyl alcohol. HCl gas was bubbled into this mixture for 10 minutes to obtain a clear solution. Nitrogen gas was bubbled through this solution to purge the excess HCl and to evaporate the ethyl alcohol until the volume of the solution was 10 mL. This solution was refrigerated for 2 hours to precipitate the product. The product was collected via vacuum filtration, was washed with ethyl ether and dried in vacuo to give 1.7 g of the hydrochloric salt (5.1 mmol, 89%).

m.p. 162-164° C.; $^1$HNMR (DMSO-d$_6$), δ (ppm): 1.36 (s, 8H), 1.53 (m, 4H), 2.71 (sex, 2H), 3.22 (q, 2H), 3.76 (s, 3H), 6.42 (m, 2H), 7.83 (d, 1H), 7.93-8.11 (s, 3H), 8.77 (t, 1H), 13.12 (bs, 1H). Elemental analysis for calculated C$_{16}$H$_{27}$N$_2$O$_3$Cl: C 58.08, H 8.23, N 8.47; found: C 57.46, H 8.24, N 8.63.

Compound 18: N-(2-hydroxy-4-methoxybenzoyl)-1,8-diaminooctane

IUPAC name: N-[2-(diethylamino)ethyl]-2-hydroxy-4-methoxybenzamide

Compound 18 was prepared by the same procedure as for compound 11 with the appropriate starting materials.

m.p. 151-153° C.; $^1$HNMR (DMSO-d$_6$), δ (ppm): 1.16-1.40 (m, 8H), 1.46 (m, 4H), 2.64 (t, 2H), 3.23 (s, 2H), 3.69 (s, 3H), 6.13 (d, 1H), 6.17 (s, 1H), 7.67 (d, 1H), 10.05 (s, 1H). KF value=0.93%. Elemental analysis for calculated C$_{16}$H$_{26}$N$_2$O$_3$*0.16H$_2$O: C 64.67, H 8.86, N 9.43; found: C 64.26, H 8.84, N 9.65.

1f: Preparation of Citrate Salts of Compounds 3,6,8 and Compounds 9,10,17

Synthesis of N-Hydroxysuccimide-O-acetylsalicylate

N-Hydroxysuccinimide (12 g, 104 mmol) was dissolved in DMF (15 mL). This solution was mixed with O-acetylsalicoyl chloride (20 g, 101 mmol) in dichloromethane (150 mL) at room temperature. Triethylamine (11 g, 109 mmol) was added dropwise to this mixture with stirring. The reaction mixture was stirred for 2 hours. The mixture was filtered to remove any insoluble material. The filtrate was collected and the solvents were evaporated in vacuo. The resulting oil was dissolved in 200 mL of ethyl acetate. Any remaining solids were removed by filtration. The filtrate was washed with 1N HCl (3×150 mL), brine (1×150 mL), 4% sodium bicarbonate (3×150 mL) and brine (1×150 mL). The ethyl acetate layer was dried over anhydrous sodium sulfate. Ethyl acetate was removed by vacuum evaporation, followed by a nitrogen purge. 20 g (72 mmol, 72%) of N-hydroxysuccimide-O-acetylsalicylate was produced.

Compound 3: N-(2-hydroxybenzoyl)-N',N'-diethylenediamine Mono-citrate

IUPAC name: N-[2-(diethylamino)ethyl]-2-hydroxybenzamide Mono-citrate

Compound 3 was prepared by the same procedure as for compound 7 with the appropriate starting materials.

m.p. 111-113° C.; $^1$HNMR (DMSO-d$_6$), δ (ppm): 1.17 (t, 6H), 2.59 (q$_{ab}$, 4H), 3.09 (m, 6H), 3.61 (q, 2H), 6.95 (m, 2H), 7.44 (t, 1H), 7.85 (d, 1H), 9.07 (s, 1H), 10.25 (bs, 2H). KF value=0.30%. Elemental analysis for calculated C$_{19}$H$_{28}$N$_2$O$_9$: C 53.27, H 6.54, N 6.54; found: C 52.96, H 6.28, N 6.37.

2-(2-hydroxybenzoyl)amino-5-(N,N-diethylamino)pentane Mono-citrate

IUPAC name: N-[5-(diethylamino)-1-methylpentyl]-2-hydroxybenzamide Mono-citrate 2-(2-hydroxybenzoyl)amino-5-(N,N-diethylamino)pentane mono-citrate was prepared by the same procedure as for compound 7 with the appropriate starting materials.

m.p. 62-64° C.; $^1$HNMR (DMSO-d$_6$), δ (ppm): 1.18 (m, 9H), 1.61 (m, 4H), 2.57 (q$_{ab}$, 4H), 3.02 (m, 6H), 4.03 (q, 1H), 4.11 (s, 1H), 6.91 (m, 2H), 7.41 (t, 1H), 7.89 (d, 1H), 8.58 (s, 1H), 10.6-11.8 (s, 2H). Elemental analysis for calculated C$_{22}$H$_{34}$N$_2$O$_9$: C 56.17, H 7.23, N 5.96; found: C 55.77, H 7.35, N 5.71.

Compound 8: N-(2-hydroxybenzoyl)-N',N'-di(n-butyl)-1,3-diaminonopropane Mono-citrate IUPAC name: N-{3-[dibutylamino]propyl}-5-chloro-2-hydroxybenzamide Mono-citrate The procedures were the same as those described for Compound 7 except for the starting materials.

m.p. 87-89° C.; $^1$HNMR (DMSO-d$_6$), δ (ppm): 0.89 (t, 6H), 1.30 (sex, 4H), 1.53 (m, 4H), 1.77 (quin, 2H), 2.59 (q$_{ab}$, 4H), 2.84-3.04 (m, 6H), 3.36 (t, 2H), 6.96 (d, 1H), 7.44 (dd, 1H), 7.90 (d, 1H), 8.97 (s, 1H). Elemental analysis for calculated C$_{19}$H$_{27}$N$_2$O$_9$Cl: C 54.08, H 6.95, N 5.26; found: C 54.13, H 7.00, N 5.10.

Compound 9: N-(2-hydroxybenzoyl)-1,12-diaminododecane Hydrogen Chloride

IUPAC name: N-(12-aminododecanyl)-2-hydroxybenzamide Hydrogen Chloride

Compound 9 was prepared by the same procedure as for compound 7 with the appropriate starting materials.

m.p. 140-142° C.; $^1$HNMR (DMSO-$d_6$), δ (ppm): 1.21 (s, 16H), 1.53 (m, 4H), 2.72 (sex, 2H), 3.27 (q, 2H), 6.89 (m, 2H), 7.37 (t, 1H), 7.7.91 (d, 1H), 7.96-8.20 (s, 3H), 8.93 (s, 1H), 12.87 (s, 1H). Elemental analysis for calculated $C_{19}H_{33}N_2O_2Cl$: C 63.94, H 9.32, N 7.85, Cl 9.93; found: C 63.33, H 9.45, N, 7.28, Cl 10.87.

Compound 10: 10-(2-hydroxybenzoylamido) Decylamine Hydrogen Chloride

IUPAC name: N-(10-aminodecyl)-2-hydroxybenzamide Hydrogen Chloride

Compound 10 was prepared by the same procedure as for compound 11 with the appropriate starting materials.

m.p. 136-138° C.; $^1$HNMR (DMSO-$d_6$), δ (ppm): 1.24 (s, 12H), 1.51 (m, 4H), 2.71 (t, 2H), 3.26 (q, 2H), 6.87 (m, 2H), 7.37 (t, 1H), 7.88 (d, 1H), 7.89-8.13 (s, 3H), 8.91 (t, 1H), 12.76 (s, 1H). Elemental analysis for calculated $C_{17}H_{29}N_2O_2Cl$: C 62.09, H 8.89, N 8.52; found: C 60.66, H 9.11, N 8.73.

Compound 17: N-(2-hydroxybenzoyl)-1,9-diaminononane

IUPAC name: N-(8-aminononyl)-2-hydroxybenzamide

Compound 17 was prepared by the same procedure as for preparing the free amine of compound 11 with the appropriate starting materials.

$^1$HNMR (DMSO-$d_6$), δ (ppm): 1.21-1.42 (m, 12H), 1.51 (m, 2H), 2.60 (t, 2H), 3.27 (t, 2H), 6.63 (t, 1H), 6.70 (d, 1H), 7.22 (t, 1H), 7.78 (d, 1H), 9.80 (s, 1H). KF value=0.91%. Elemental analysis for calculated $C_{16}H_{26}N_2O_2$ (0.91% $H_2O$): C 68.61; H 9.33; N 9.97; Found: C 68.54, H 9.41, N 10.31.

1g: Preparation of Compound 12

A 20 mL scintillation vial was charged with 3,5-dibromosalicylic acid (1.299 g, 4.39 mmol), 1-[3-(dimethylamino)propyl]-3-ethylcarbodiimide*HCl (0.99 g, 5.2 mmol) and 1-hydroxybenzotriazole hydrate (0.79 g, 5.8 mmol). 1-(3-Aminopropyl)imidazole (476 µl, 3.99 mmol) was added by autopipet. THF (10 mL) was added, the vial was capped, and placed on an orbital shaker overnight at 60° C. The heat was turned off and the vial was allowed to cool back to room temperature. Trisamine resin (200 mg, 0.85 mmol) was added and the vial placed back on the orbital shaker for 4 hours. Amberlyst-15 (2 g, 9.4 mmol) and Amberlyst-21 (2 g, 9.4 mmol) ion-exchange resins were added to the vial along with DCM (5 mL) to suspend the resins. The vial was placed back on the orbital shaker overnight. The reaction mixture was filtered and the resins were rinsed with DCM (2×5 mL). The combined filtrates were placed under a nitrogen stream overnight. 2.3985 g of material was recovered.

LC-MS: rt=2.39 min, 89%, M+H=404

1h: Preparation of Compound 13

A 20 mL scintillation vial was charged with 3,5-dichlorosalicylic acid (0.9082 g, 4.39 mmol), 1-[3(dimethylamino) propyl]-3-ethylcarbodiimide*HCl (0.99 g, 5.2 mmol) and 1-hydroxybenzotriazole hydrate (0.79 g, 5.8 mmol). 1-(3-Aminopropyl)imidazole (476 µl, 3.99 mmol) was added by autopipet. THF (10 mL) was added, the vial was capped, and placed on an orbital shaker overnight at 60° C. The heat was turned off and the vial was allowed to cool back to room temperature. Trisamine resin (200 mg, 0.85 mmol) was added and the vial placed back on the orbital shaker for 4 hours. Amberlyst-15 (2 g, 9.4 mmol) and Amberlyst-21 (2 g, 9.4 mmol) ion-exchange resins were added to the vial along with DCM (5 mL) to suspend the resins. The vial was placed back on the orbital shaker overnight. The reaction mixture was filtered and the resins were rinsed with DCM (2×5 mL). The combined filtrates were placed under a nitrogen stream overnight. 2.0343 g of material was recovered.

LC-MS: rt=2.24 min, 79%, M+H=315

1i: Preparation of Compound 14

A 20 mL scintillation vial was charged with 3,5-diiodosalicylic acid (1.700 g, 4.39 mmol), 1-[3(dimethylamino)propyl]-3-ethylcarbodiimide*HCl (0.99 g, 5.2 mmol) and 1-hydroxybenzotriazole hydrate (0.79 g, 5.8 mmol). 1-(3-Aminopropyl)imidazole (476 µl, 3.99 mmol) was added by autopipet. THF (10 mL) was added, the vial was capped, and placed on an orbital shaker overnight at 60° C. The heat was turned off and the vial was allowed to cool back to room temperature. Trisamine resin (200 mg, 0.85 mmol) was added and the vial placed back on the orbital shaker for 4 hours. Amberlyst-15 (2 g, 9.4 mmol) and Amberlyst-21 (2 g, 9.4 mmol) ion-exchange resins were added to the vial along with DCM (5 mL) to suspend the resins. The vial was placed back on the orbital shaker overnight. The reaction mixture was filtered and the resins were rinsed with DCM (2×5 mL). The combined filtrates were placed under a nitrogen stream overnight. 2.7305 g of material was recovered.

LC-MS: rt=2.62 min, 84%, M+H=498

1j: Preparation of Compound 15

A 20 mL scintillation vial was charged with 3,5-dibromosalicylic acid (1.299 g, 3.8 mmol), 1-[3-(dimethylamino)propyl]-3-ethylcarbodiimide*HCl (0.84 g, 4.39 mmol) and 1-hydroxybenzotriazole hydrate (0.59 g, 4.38 mmol). 4-(3-Aminopropyl)morpholine (506 µl, 3.47 mmol) was added by autopipet. THF (10 mL) was added, the vial was capped, and placed on an orbital shaker overnight at 60° C. The heat was turned off and the vial was allowed to cool back to room temperature. Trisamine resin (200 mg, 0.85 mmol) was added and the vial placed back on the orbital shaker for 4 hours. Amberlyst-15 (2 g, 9.4 mmol) and Amberlyst-21 (2 g, 9.4 mmol) ion-exchange resins were added to the vial along with DCM (5 mL) to suspend the resins. The vial was placed back on the orbital shaker overnight. The reaction mixture was filtered and the resins were rinsed with DCM (2×5 mL). The combined filtrates were placed under a nitrogen stream overnight. 2.103 g of material was recovered.

LC-MS: rt=2.36 min, 74%, M+H=423

1k: Preparation of Compound 16

A 20 mL scintillation vial was charged with 3,5-dichlorosalicylic acid (0.786 g, 3.8 mmol), 1-[3-(dimethylamino)propyl]-3-ethylcarbodiimide*HCl (0.84 g, 4.39 mmol) and 1-hydroxybenzotriazole hydrate (0.59 g, 4.38 mmol). 4-(3-Aminopropyl)morpholine (506 µl, 3.47 mmol) was added by autopipet. THF (10 mL) was added, the vial was capped, and placed on an orbital shaker overnight at 60° C. The heat was turned off and the vial was allowed to cool back to room temperature. Trisamine resin (200 mg, 0.85 mmol) was added and the vial placed back on the orbital shaker for 4 hours. Amberlyst-15 (2 g, 9.4 mmol) and Amberlyst-21 (2 g, 9.4 mmol) ion-exchange resins were added to the vial along with DCM (5 mL) to suspend the resins. The vial was placed back on the orbital shaker overnight. The reaction mixture was filtered and the resins were rinsed with DCM (2×5 mL). The combined filtrates were placed under a nitrogen stream overnight. 1.648 g of material was recovered.

LC-MS: rt=2.23 min, 75%, M+H=334

1k: Alternate Preparations of Compounds 12,13,14,15,16

Compounds 12, 13, 14, 15, and 16 are synthesized by the same procedure described to make compound 7 using the appropriate starting materials.

EXAMPLE 2

2A: Insulin—Oral Delivery

Oral dosing (PO) compositions of delivery agent compound and human zinc insulin (minimum 26 IU/mg available from Calbiochem—Novabiochem Corp, La Jolla, Calif.) were prepared in deionized water. Typically, 500 mg of delivery agent compound was added to 1.5 ml of water. The solution was vortexed, then heated (about 37° C.) and sonicated. The pH was adjusted to about 7 to 8.5 with NaOH or HCl. Additional NaOH was added, if necessary, to achieve uniform solubility, and the pH readjusted to about 7 to 8.5. Water was then added to bring the total volume to about 2.4 ml and vortexed. About 1.25 mg insulin from an insulin stock solution (15 mg/ml made from 0.5409 g insulin and 18 ml deionized water, adjusting with HCl and NaOH to pH 8.15 and to obtain a clear solution using 40 ml concentrated HCl, 25 ml 10N NaOH and 50 ml 1N NaOH) was added to the solution and mixed by inverting. The solution may be used in the dosing protocol immediately, or alternatively, the solution may be placed into a 37° C. water bath for one hour prior to dosing. The final delivery agent compound dose, insulin dose and dose volume amounts are listed below in Table 1.

The typical dosing and sampling protocols were as follows. Male Sprague-Dawley rats weighing between about 200-250 g were fasted for 24 hours and administered ketamine (44 mg/kg) and chlorpromazine (1.5 mg/kg) 15 minutes prior to dosing and again as needed to maintain anesthesia. A dosing group of five animals was administered one of the dosing solutions. For oral dosing, an 11 cm Rusch 8 French catheter was adapted to a 1 ml syringe with a pipette tip. The syringe was filled with dosing solution by drawing the solution through the catheter, which was then wiped dry. The catheter was placed down the esophagus leaving 1 cm of tubing past the incisors. The dosing solution was administered by pressing the syringe plunger.

Blood samples were collected serially from the tail artery, typically at time=15, 30, 60, 120 and 180 minutes. Serum insulin levels were determined with an Insulin ELISA Test Kit (Kit # DSL-10-1600 from Diagnostic Systems Laboratories, Inc., Webster, Tex.), modifying the standard protocol in order to optimize the sensitivity and linear range of the standard curve for the volumes and concentrations of the samples used in the present protocol. Serum human insulin concentrations (µU/ml) were measured for each time point for each of the five animals in each dosing group. The five values for each time point were averaged and the results plotted as serum insulin concentration versus time. (Previous experiments revealed no measurable levels of human insulin following oral dosing with human insulin alone.) The maximum (peak) and the area under the curve (AUC) are reported below in Table 1.

TABLE 1

Insulin - Oral Delivery

| Delivery Agent Compound | Delivery Agent Compound Dose (mg/kg) | Insulin Dose (mg/kg) | Volume dose (ml/kg) | Mean Peak Serum [INS] ± SD |
|---|---|---|---|---|
| 15 | 200 | 0.25 | 1 | 60.42 ± 117.16 |
| 16 | 200 | 0.25 | 1 | 61.27 ± 116.59 |
| 12 | 200 | 0.25 | 1 | 83.4 ± 14.69 |
| 13 | 200 | 0.25 | 1 | 76.8 ± 6.80 |

2B: Biotinylated Ribonuclease A (bRNase A) Oral Delivery

Oral gavage (PO) dosing solutions of delivery agent compound and bRNase A (Sigma (Milwaukee, Wis.): Ribonuclease A Type XII-A from bovine pancreas) in deionized water were prepared by mixing. The delivery agent compound solution was prepared in phosphate buffer and stirred. If necessary, the pH of the mixture was adjusted upwards by the addition of aliquots of NaOH of an appropriate normality until the delivery agent compound was completely dissolved. The final pH of the dissolved delivery agent compound was between 7.5 and 9.5. The final dosing solutions were prepared by mixing 9 volumes of the delivery agent compound solution with 1 volume of a bRNase A stock solution (20 mg bRNase A in phosphate buffered saline (PBS)). Final concentrations were 150 mg/ml delivery agent compound and 2 mg/ml bRNase A.

The dosing and sampling protocols were as follows. Male Sprague-Dawley rats weighing 200-250 g were fasted for 24 hours and administered ketamine (44 mg/kg) and chlorpromazine (1.5 mg/kg) 15 minutes prior to dosing and again as needed to maintain anesthesia. A dosing group of five animals was administered one of the dosing solutions in the following manner. An 11 cm Rusch 8 French catheter was adapted to a 1 ml syringe with a pipette tip. The syringe was filled with dosing solution by drawing the solution through the catheter, which was then wiped dry. The catheter was placed down the esophagus leaving 1 cm of tubing past the incisors. The dosing solution was administered by pressing the syringe plunger. Blood samples were collected serially from the tail artery at 15, 30, 45, 60 and 90 minutes. Serum bRNase A concentrations were quantified by a modified immunoassay as described below.

Biotinylation of Ribonuclease A

To label each of the RNase A molecules with one biotin molecule, the ratio of the activated biotin was maintained at 3 moles biotin/1 mole RNase A. In a representative biotinylation reaction 500 mg of RNase A was dissolved in 20 ml of 50 mM NaHCO$_3$, pH 7.6. 57.08 mg of EZ-Link Sulfo-NHS-LC-LC Biotin (Pierce Chemical Company, Rockford, Ill.) was added to the solution, dissolved and allowed to stand on ice for 2 hours. The reaction mix was then dialyzed (10,000 MW cutoff dialysis membrane (Pierce, Rockford, Ill.)) against 4 liters of PBS at 4° C. overnight. The reaction mix was place in 4 liters of fresh PBS and dialyzed for an additional 4 hours. The dialyzed bRNase A was removed from the dialysis membrane, diluted to a final volume of 25 ml with PBS (final concentration of bRNase A=20 mg/ml), and stored a 4° C.

Assay of Serum Levels of Orally Administered bRNase A

In general 100 µl aliquots of the rat sera collected at the various time points were placed in the appropriate wells of a 96 well Reacti-Bind Streptavidin Coated Polystyrene Plates (Pierce). After a 2 hour incubation period the plates were washed and then incubated with a polyclonal rabbit anti-RNase A (Chemicon, Pittsburgh, Pa.). After washing, the plates were incubated for 2 hours with a polyclonal goat anti-rabbit IgG (Chemicon, Pittsburgh, Pa.) conjugated to alkaline phosphatase. The plates were washed after the incubation and the amount of initially captured bRNase A is detected by the addition of para-nitrophenyl phosphate (a substrate for alkaline phosphatase) (Pierce, Rockford, Ill.). The amount of bRNase A circulating in the original rat sera is quantitated by comparison with a standard curve of bRNAse A which extends from 1000-0.1 ng/mL in fifteen two-fold dilutions. The maximum±standard deviation is given in Table 2 below.

TABLE 2

Oral Delivery of RNAase

| Delivery Agent Compound | Delivery Agent Compound Dose (mg/kg) | bRNAase Dose (mg/kg) | Volume dose (ml/kg) | Mean Peak Serum ng/ml |
| --- | --- | --- | --- | --- |
| 1 | 150 | 1 | 1 | 2.38 ± 2.2 |
| 3 | 150 | 1 | 1 | 2.98 ± 1.66 |

2c: Oral Delivery of BIBN4096BS

Oral gavage (PO) dosing solutions of delivery agent compound and the Calcitonin gene-related peptide antagonist, 1-Piperidinecarboxamide. N-[2-[[5-amino-1-[[4-(4-pyridinyl)-1-piperazinyl]carbonyl]pentyl]amino]-1-[(3,5-dibromo-4-hydroxyphenyl)methyl]-2-oxoethyl]-4(1,4-dihydro-2-oxo-3(2H0-quinazolinyl)-.[R-(R*,S*)] (BIBN4096BS) in water were prepared. Typically, a solution of the delivery agent compound was prepared in water and stirred. The final dosing solutions were prepared by mixing the delivery agent compound with a BIBN4096BS stock solution and diluting to the desired volume (usually 1.0 mL). If necessary, the pH of the mixture was adjusted by the addition of aliquots of aqueous hydrochloric acid solution of an appropriate normality until the final pH of the dosing solution was below 7.0. The final compound amounts per dose were 25 mg/kg of BIBN4096BS, 200 mg/kg of delivery agent compound, in a total volume of 1 mL/kg.

The typical dosing and sampling protocols were as follows. Male Sprague-Dawley rats weighing between 200-250 g were fasted for 24 hours and administered ketamine (44 mg/kg) and chlorpromazine (1.5 mg/kg) 15 minutes prior to dosing. A dosing group of five rats was administered one of the dosing solutions. For oral gavage (PO) dosing, an 11 cm Rusch 8 French catheter was adapted to a 1 mL syringe with a pipette tip. The syringe was filled with dosing solution by drawing the solution through the catheter, which was then wiped dry. The catheter was placed down the esophagus leaving 1 cm of tubing past the incisors. Solution was administered by pressing the syringe plunger. Blood samples were collected serially from the tail artery, typically at time=0, 15, 30, 45, and 60 minutes for oral. Plasma BIBN4096BS concentrations were quantified by using a liquid chromatography/mass spectrometry/mass spectrometry assay method using UV detection. The standard range for the assay was 5-2,000 ng/mL. Previous studies indicated baseline values of about 10 ng/mL. The maximum is reported below in Table 3.

TABLE 3

Oral BIBN4096BS Delivery

| Delivery Agent Compound | Delivery Agent Compound Dose (mg/kg) | BIBN4096BS Dose (mg/kg) | Volume dose (ml/kg) | Mean Peak Serum ng/ml |
| --- | --- | --- | --- | --- |
| 1 | 200 | 25 | 1 | 28 ± 19 |
| 4 | 200 | 25 | 1 | 23 ± 14 |
| 2 | 200 | 25 | 1 | 453 ± 300* |
| 5 | 200 | 25 | 1 | 402 ± 608* |
| 13 | 200 | 25 | 1 | 12 ± 3.6 |
| 15 | 200 | 25 | 1 | 0 |
| 16 | 200 | 25 | 1 | 15 ± 8.1 |

*some dosing solutions were at a pH ≧ 8.0

The above mentioned patents, applications, test methods, and publications are hereby incorporated by reference in their entirety.

Many variations of the present invention will suggest themselves to those skilled in the art in light of the above detailed description. All such obvious variations are within the fully intended scope of the appended claims.

What is claimed is:

1. A compound selected from the group consisting of compounds 1-18:

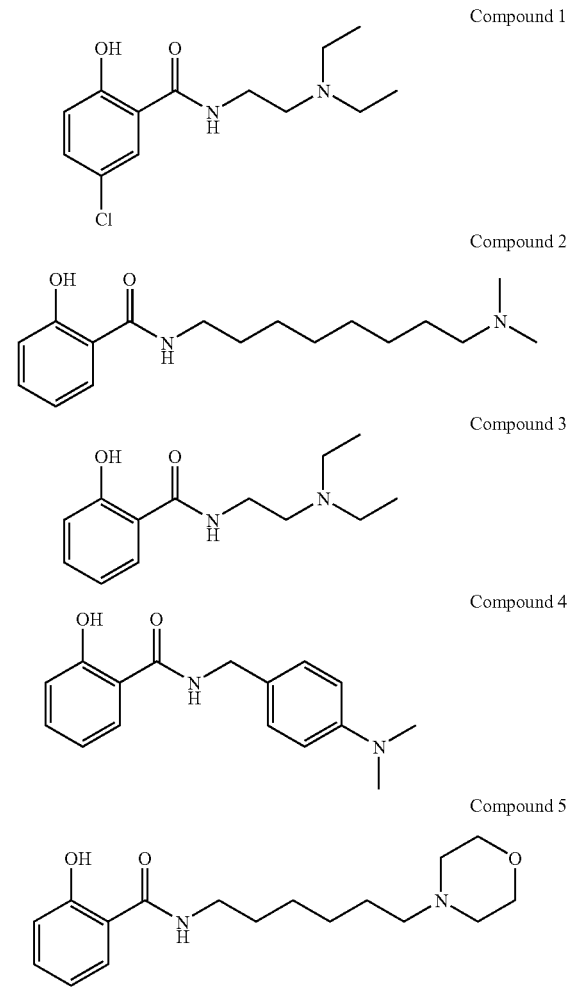

-continued

Compound 6
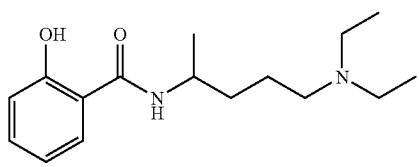

Compound 7
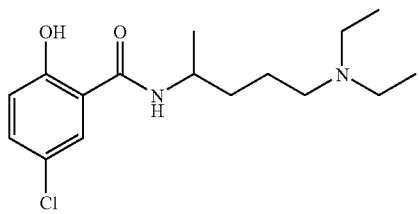

Compound 8
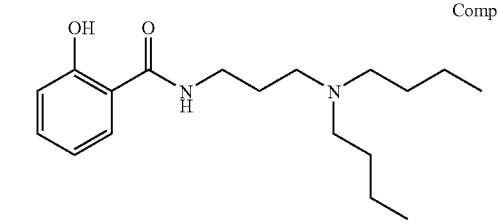

Compound 9
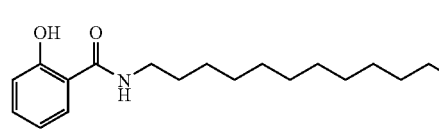

Compound 10
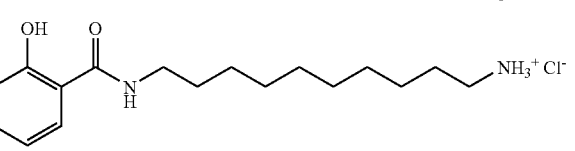

Compound 11
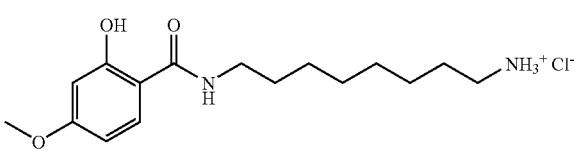

Compound 12
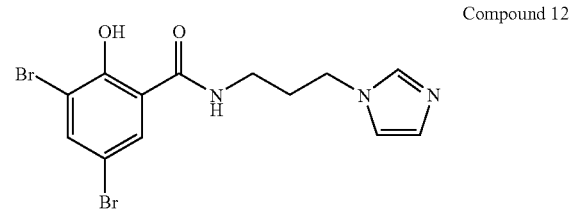

Compound 13
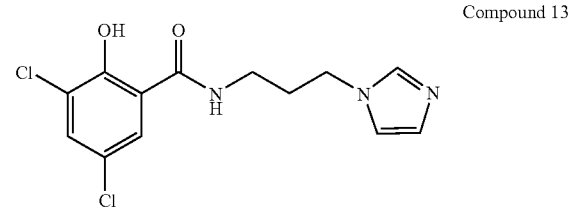

-continued

Compound 14
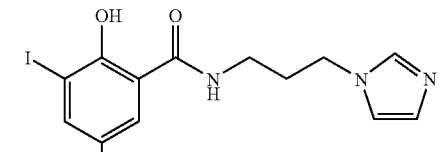

Compound 15
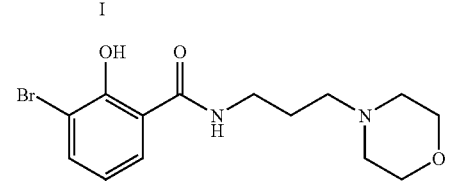

Compound 16
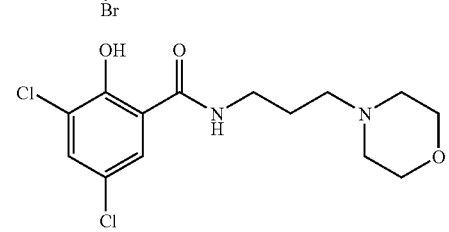

Compound 17
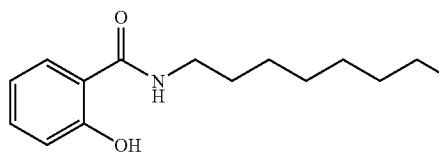

Compound 18
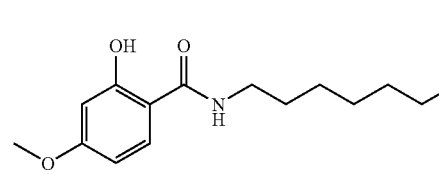

and salts thereof.

2. A pharmaceutical composition comprising:
(A) a biologically active agent selected from BIBN-4096BS, growth hormones, human growth hormones, recombinant human growth hormones (rhGH), bovine growth hormones, porcine growth hormones, α-interferon, β-interferon, γ-interferon, interleukin-1, interleukin-2, insulin, porcine insulin, bovine insulin, human insulin, human recombinant insulin, insulin-like growth factor (IGF), IGF-1, heparin, unfractionated heparin, heparinoids, dermatans, chondroitins, low molecular weight heparin, very low molecular weight heparin, ultra low molecular weight heparin, calcitonin, salmon calcitonin, eel calcitonin, human calcitonin; erythropoietin (EPO), somatostatin, adrenocorticotropin, gonadotropin releasing hormone, oxytocin, glucocerebrosidase, thrombopoeitin, fligrastim, prostaglandins, cyclosporin, vasopressin, cromolyn sodium, sodium chromoglycate, disodium chromoglycate, vaneomycin, desferrioxamine (DFO), parathyroid hormone (PTH), fragments of PTH, and any combination thereof; and (B) at least one compound selected from
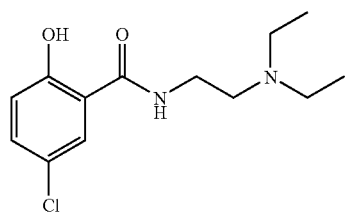
Compound 1
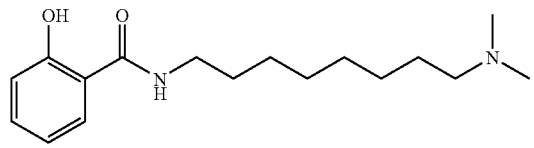
Compound 2
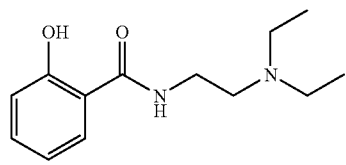
Compound 3
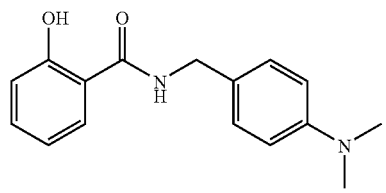
Compound 4
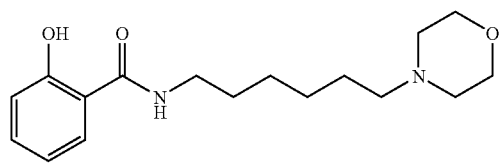
Compound 5
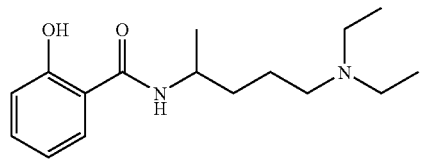
Compound 6
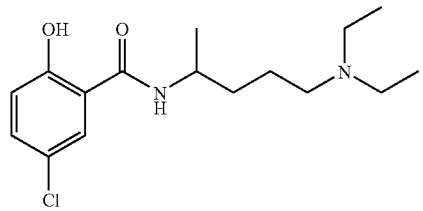
Compound 7
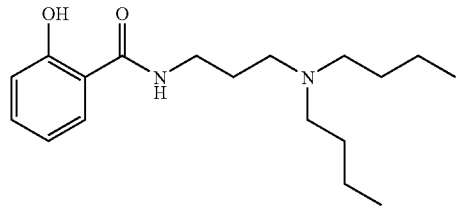
Compound 8

-continued
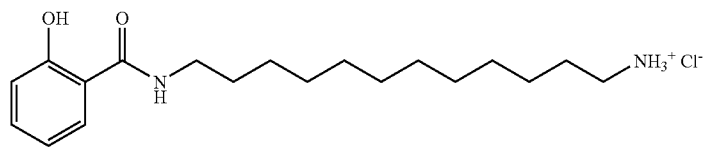
Compound 9
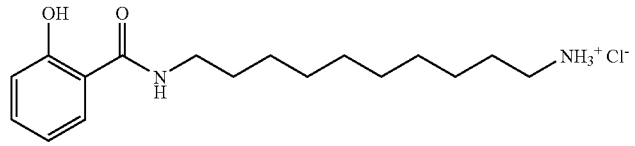
Compound 10
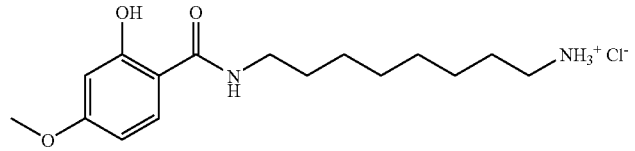
Compound 11
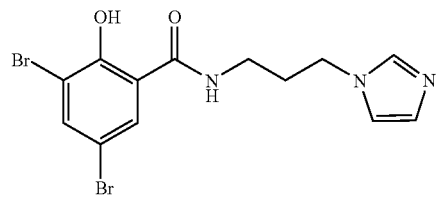
Compound 12
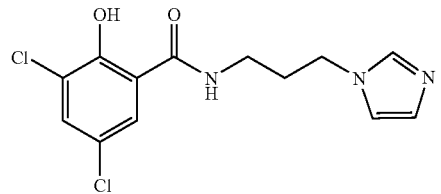
Compound 13
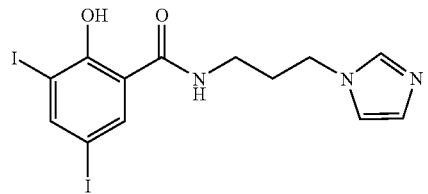
Compound 14
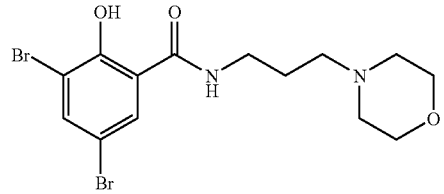
Compound 15
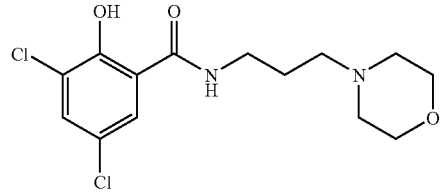
Compound 16

-continued

Compound 17

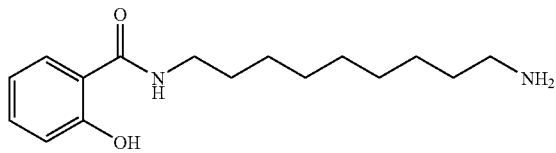

Compound 18

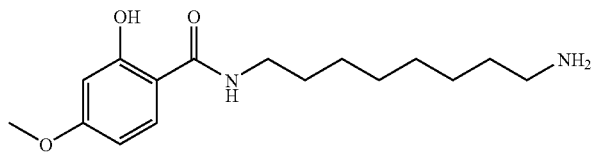

and salts thereof.

3. The composition of claim 2, wherein the biologically active agent comprises insulin, BIBN-4096BS, calcitonin, parathyroid hormone, erythropoietin, growth hormones or any combination thereof.

4. The composition of claim 2, wherein the biologically active agent comprises BIBN-4096BS.

5. The composition of claim 2, wherein the biologically active agent comprises insulin.

6. A dosage unit form comprising:
(A) the composition of claim 2; and
(B) (a) an excipient,
(b) a diluent,
(c) a disintegrant,
(d) a lubricant,
(e) a plasticizer,
(f) a colorant,
(g) a dosing vehicle, or
(h) any combination thereof.

7. The dosage unit form of claim 6, wherein the biologically active agent comprises insulin, BIBN-4096BS, calcitonin, parathyroid hormone, erythropoietin, human growth hormones or any combination thereof.

8. The dosage unit form of claim 6, wherein the active agent comprises recombinant BIBN-4096BS.

9. The dosage unit form of claim 6, wherein the active agent comprises insulin.

10. The dosage unit form of claim 6, wherein the dosage unit form comprises a dosing vehicle comprising a tablet, a capsule, a powder, or a liquid.

11. The dosage unit form of claim 6, wherein the dosing vehicle is liquid selected from the group consisting of water, 1,2-propane diol, ethanol, and any combination thereof.

* * * * *